United States Patent [19]
Liu et al.

[11] Patent Number: 6,013,070
[45] Date of Patent: Jan. 11, 2000

[54] APPARATUS USING LASER PUMP SOURCE FOR STERILIZATION

[75] Inventors: Chuanlin Liu; Mingzhang Wang; Chengfu Jia; Baode Xu; Xiuhua Li; Zhenqian Zhou; Jinru Xie; Huanmin Gou; Jijun Shao, all of Shandong, China

[73] Assignees: Oingdao Tongda Technology Developing (Group) Co., Ltd.; Oingdao First Convalescent Hospital of Pla Jinanjunqu, both of Oingdao, China

[21] Appl. No.: 08/983,272

[22] PCT Filed: Jun. 26, 1995

[86] PCT No.: PCT/CN95/00052

§ 371 Date: Apr. 27, 1998

§ 102(e) Date: Apr. 27, 1998

[87] PCT Pub. No.: WO97/01361

PCT Pub. Date: Jan. 16, 1997

[51] Int. Cl.[7] ........................................................ A61L 2/10
[52] U.S. Cl. .................................................. 606/1; 422/22
[58] Field of Search ....................... 606/3, 1, 10; 422/22, 422/24; 607/88, 89, 94; 433/215

[56] References Cited

U.S. PATENT DOCUMENTS

| | | | |
|---|---|---|---|
| 4,115,280 | 9/1978 | Pratt, Jr. | 250/527 |
| 5,240,675 | 8/1993 | Wilk et al. | 600/101 |
| 5,571,488 | 11/1996 | Beerstecher et al. | 422/297 |
| 5,637,877 | 6/1997 | Sinofsky | 422/24 |
| 5,744,094 | 4/1998 | Castberg et al. | 422/24 |
| 5,820,821 | 10/1998 | Kawagoe et al. | 422/22 |

*Primary Examiner*—John P. Leubecker
*Attorney, Agent, or Firm*—Brinks Hofer Gilson & Lione

[57] ABSTRACT

The sterilization is performed using flashing pulses of laser pump source. The apparatus comprises a control circuit, a washing and drying mechanism, and an integrated ball type sterilization mechanism. The washing and drying mechanism includes a device for injecting pressurized water, a device for injecting pressurized air, and a device for heating the compressed air. The integrated ball type mechanism is shaped as a spheroid and the inner surface of the spherical cavity is a high-reflectivity mirror surface. The laser pump source is located within the spherical cavity.

2 Claims, 3 Drawing Sheets

APPARATUS USING LASER PUMP SOURCE FOR STERILIZATION

FIELD OF THE INVENTION

The present invention relates to a sterilization method and apparatus, particularly to a sterilization method and apparatus for sterilizing precision and precious medical instruments. The present invention is especially useful for medical instruments which cannot be sterilized by conventional methods. Such medical instruments include high speed hand drills that are used in an alimentary canal department, detecting heads for supersonic diagnostic sets and medical instrument used for optics. The present invention can also be used for sterilizing sanitary equipment used in hotels and other public places.

BACKGROUND OF THE INVENTION

There are presently two general types of sterilization methods that are used for medical instruments. First, the conventional physical sterilization methods, for example, high pressure dry heating method, boiling method, microwave sterilization method and ultraviolet ray sterilization method. The second conventional type is the chemical sterilization method, for example, immersing medical instrument to be sterilized in liquids such as peracetic acid, ethylene oxide, glutaraldehyde, formalin alcohol or hibitane acetate and other such chemicals.

When conventional sterilization methods, such as high pressure dry heating and boiling methods are utilized to sterilize, for example, the hand drills that are used in alimentary canal departments, parts of the drill such as the bearing or rubber packing sheets, will be damaged as a result of being exposed to high temperature. If the microwave sterilization method is used, discharge will occur because of the metal parts that are present in the hand drill. When ultraviolet rays irradiation is used for the sterilization process, dimer is formed following the ultraviolet rays irradiation. The dimer is dissolvable under sunlight and bacterium immediately revives. This process is called photo-vivification and is well known in medical practice, hence, sterilization using ultraviolet ray irradiation is unreliable.

If medical instruments are immersed in peracetic acid for the purpose of sterilization, the metal parts of the instrument will seriously corrode. When medical instruments are immersed in glutaraldehyde or ethylene oxide for the purpose of sterilization, any residue of these substances that remain on the surface of the medical instruments will form new antigen which, when it enters into the human body's bloodstream, will cause anaphylactic shock. Although formalin alcohol or hibitane acetate is used to immerse the medical instrument to be sterilized, only part of the pathogen microbes can be selectively destroyed, hence, this method of sterilization is unreliable for some viruses.

Therefore, an object of the present invention is to provide a new sterilization method and an apparatus for medical instruments and or equipment which not only shortens the time required for sterilization but also does not damage the sterilized instruments. Moreover, there is no antigen remaining on the surface of the sterilized instruments.

SUMMARY OF THE INVENTION

Accordingly, a sterilization method using laser pump source according to the present invention is provided which comprises the steps of:

(1) washing the object to be sterilized in the mixture flow of gas and water;

(2) drying the object to be sterilized;

(3) exposing the object to be sterilized to laser pump source, so that sterilization is performed using flashing pulses of laser pump source to radiate it; and (4) wrapping the sterilized object in an aseptic jacket. Preferably, the laser pump source flashes 6 times at intervals of one second between each flash.

In accordance with the present invention, there is provided a sterilization apparatus that uses a laser pump source. This apparatus includes a control circuit, a washing and drying means and an integrated ball for sterilization.

The washing and drying means includes:

a pressurization water source;

a compressed-air source and a compressed-air heater;

a barrel cavity having a ventilator on its upper side and a sewage outlet on its bottom side;

a number of water-spray-tubes extending longitudinally inwardly from one end of the barrel cavity, the water spray tubes being connected to a pressurized water container, and each water-spray-tube having a plurality of spray holes; and a loading cover assembly provided for the opening in the barrel cavity which is located opposite to said one end of the barrel cavity. The loading cover assembly comprises an air-jet orifice-plate, a cup-shaped joint fixed to the air-jet orifice-plate, a handle for the cavity cover and a heat isolating gasket for sealing purposes; and said air-jet orifice-plate has a plurality of air-jet apertures and an air-jet tube mounted in its center upon which the object or objects to be sterilized are arranged.

When the loading cover assembly is in its proper position on the periphery of said cup-shaped joint, it is provided with a compressed-air joint that is connected with a compressed-air source, and a positioning pin that indicates that the loading cover assembly has been fixed and sealed in its correct position.

When the loading cover assembly has been fixed and sealed in its proper position, the cup-shaped joint and the air-jet orifice-plate of said loading cover assembly are arranged inside of a ring-shaped member which is mounted on the opening end of the barrel cavity. The ring-shaped member has a radial throughhole which is used for inserting the compressed-air tube and is located in a position corresponding to said compressed-air joint. The compressed-air tube can be inserted into said throughhole by means of a swing-arm apparatus so as to be connected with the compressed-air joint.

The integrated ball for sterilization includes:

an upper semi-spherical and a lower semi-spherical cavities members that are jointed together through a joint in a sealed manner;

a cavity opening located on the joint of the semi-spherical members;

a laser pump source lamp fixed inside the spherical cavity by means of several support rods;

two electrodes of the lamp protrude outside of the spherical cavity, and through the lower side of the spherical cavity, a trigger high voltage connection led to the upper portion of the lamp; and a handle provided on the outer side of the cavity cap, the shape of which matches that of the cavity opening, positioning pins located on the peripheral surface of the cavity cap, and on the inner side of the cavity cap there is a movable intermediate joint that extends in the axial direction for mounting the object to be sterilized.

The laser pump source could, preferably, be a pulse xenon lamp, a pulse krypton lamp or a pulse tungsten halide lamp.

When in use, the compressed-air tube is pulled out from the throughhole formed in the ring-shape member by means of the swing-arm apparatus. The loading cover assembly is axially withdrawn and the object to be sterilized is arranged around the air-jet tube of the loading cover assembly. Then, the loading cover assembly is mounted into the ring-shaped member until the positioning pin arrives at its proper position. The compressed-air tube is inserted into the radial throughhole by means of the swing-arm apparatus and is connected to the compressed-air joint located on the periphery of the joint mounted inside the loading cover assembly. Then, the pressurized water container and the compressed-air source are connected. Pressurized water is then injected from the spray holes of the water spray tube and compressed-air from the air-jet apertures of the air-jet orifice-plate and from the air-jet tube to thereby wash the object to be sterilized. After washing is completed, the spray of pressurized water is stopped. In the meantime, the spraying of compressed-air is continued. The compressed-air is heated to a temperature somewhat higher than the room temperature, for instance, 50° C. Therefore the object to be sterilized is scoured by the heated compressed-air and is then dried.

The washed and dried object to be sterilized is then mounted on the cavity cap inside the integrated ball for sterilization. The cavity opening is closed by the cavity cap in a sealed manner. The laser pump source is started such that it flashes a total of 6 times at intervals of one second between each flash. The cavity cap is then opened, and the sterilized object is wrapped in an aseptic jacket. The sterilization procedures of the object according to the present invention has now been completed.

The sterilization principle of this sterilization method and apparatus using laser pump source according to the present invention combines the following sterilization principles: high-intensity irradiation, instant high temperature sterilization, induced skin current sterilization, alternative electromagnetic field sterilization, vacuum ultraviolet rays sterilization and pulse mechanic effect sterilization.

DESCRIPTION OF THE ACCOMPANYING DRAWINGS

DESCRIPTION OF THE PREFERRED EMBODIMENTS

The sterilization apparatus using laser pump source, according to the present invention, will now be described in detail with reference to the accompanying drawings.

Figure 3:
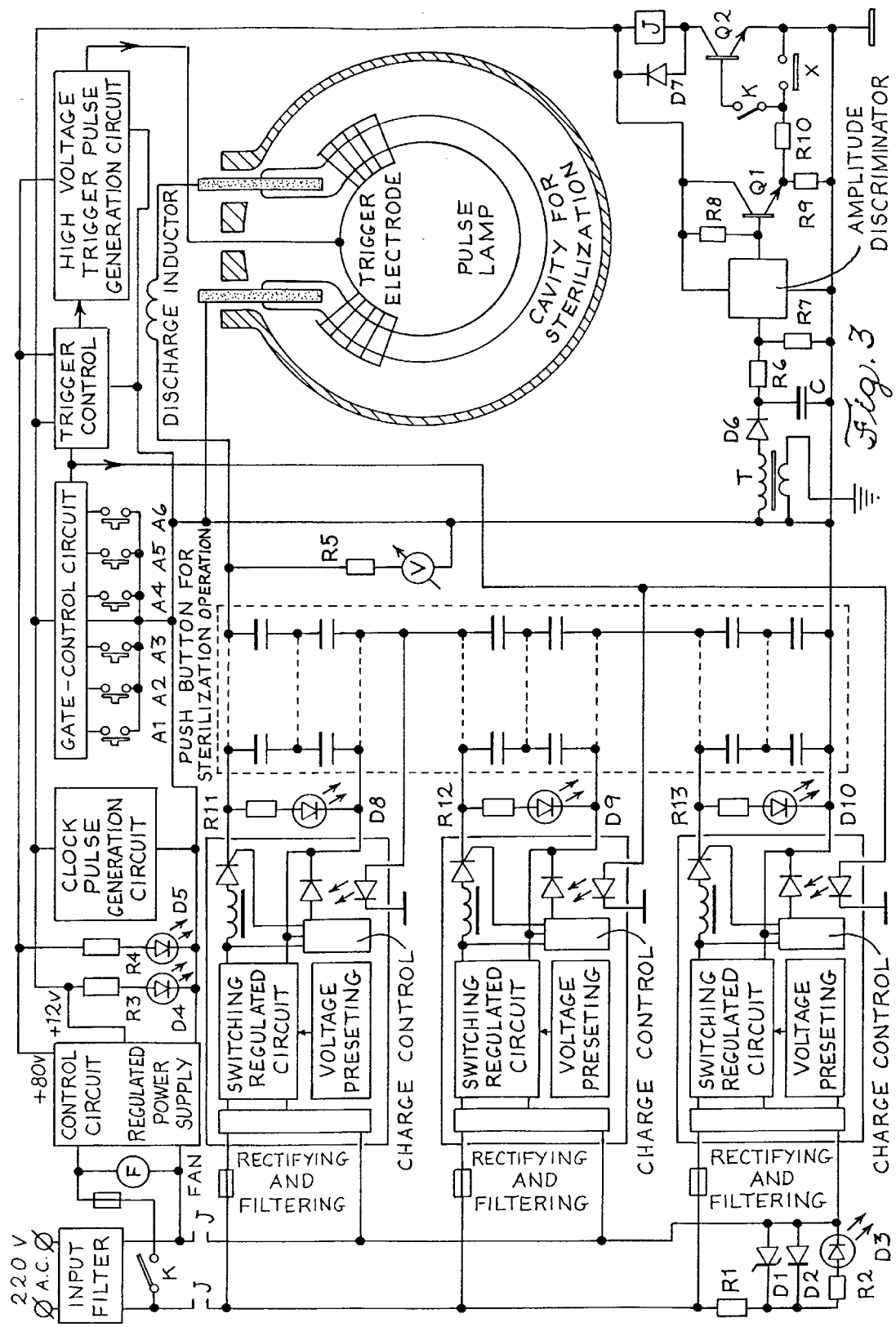
FIG. 3 is the control circuit for the sterilization apparatus.

The control circuit illustrated in FIG. 3 is standard available technology and is not a part of this invention. A detailed discussion of this standard available technology is not necessary for a full understanding of this invention and thus has not been included.

Figure 1:
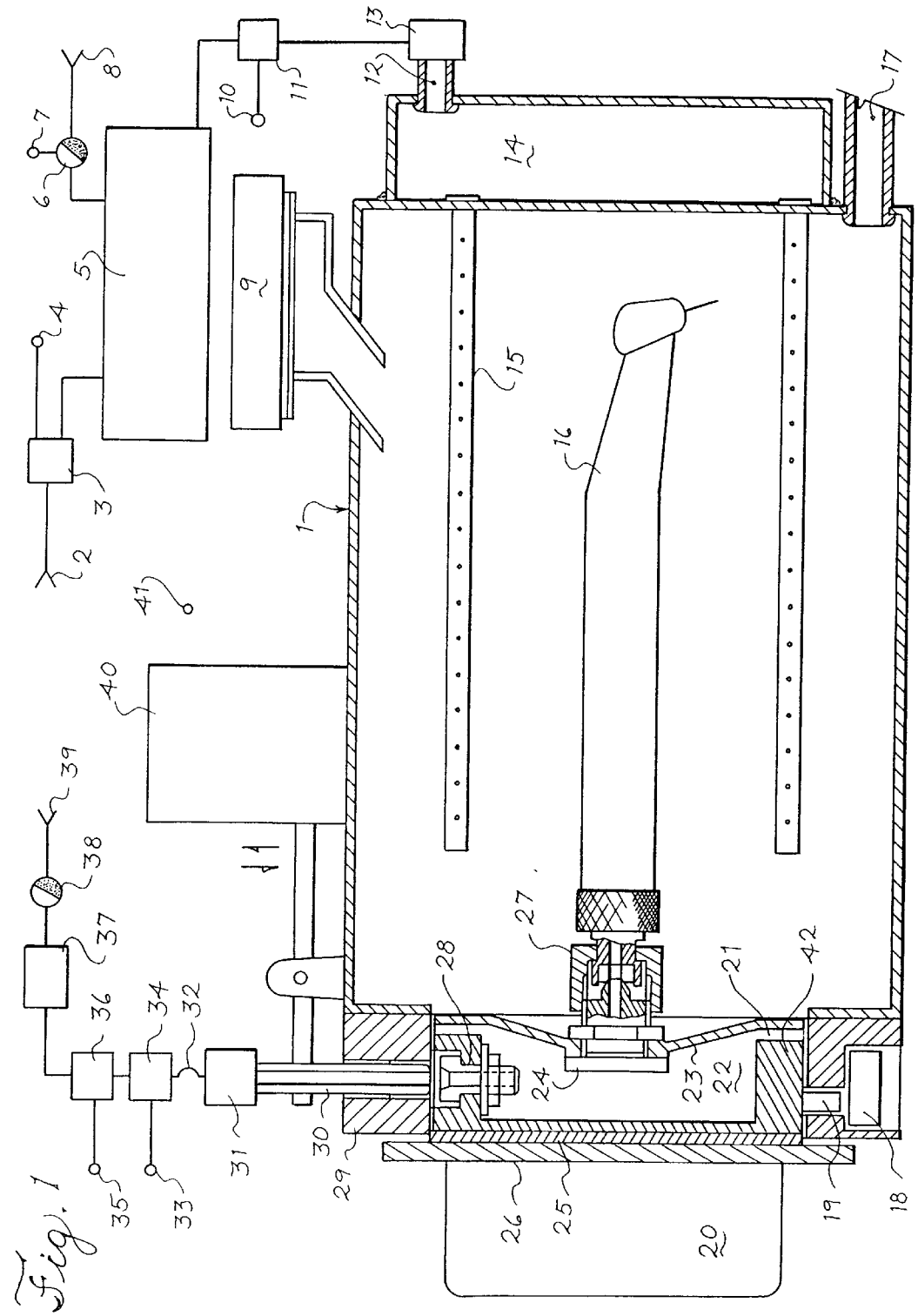
FIG. 1 is a cross section view of the washing and drying apparatus that is used in the sterilization process.

FIG. 1 illustrates the washing and drying mechanisms of the sterilization according to the present invention. The pressurized water container 5, which is a part of the washing means, includes a pressurized water source to which water is supplied through a tap water inlet 8 that is controlled by an electric control water valve 6. The power connection for the electric control water valve 6 is designated by the number 7. Compressed-air is supplied into the pressurized water container 5 through a compressed air inlet 2 which is under the combined control of the electric control valve 3 and the power connection 4 that is joined to power connection 7. Accordingly, the water in water container 5 is pressurized and a pressurized water source is available.

A compressed-air inlet 39 and valve 38 are connected through a filter 37 to an electric control valve 36 and then, in turn, to an electric control valve 36, heater 34, hose 32, joint 31 and the compressed-air tube 30. The heater 34 and valve 36 are provided with power connections 33 and 35, respectively.

The barrel cavity 1 has a ventilator 9 on its upper side and a sewage outlet 17 on its bottom side. A high pressure water tank 14 is formed by a sealed cover at one end of the barrel cavity 1. The pressurized water is supplied to the tank 14 through joint 13 and high pressure water inlet 12. A number of water spray tubes 15 each having a plurality of spray holes formed therein are fixed to the end wall of the barrel cavity 1. These water spray tubes 15 are arranged along a circle about the axis of the barrel cavity 1 and extend longitudinally inside the barrel cavity 1. The water spray tubes 15 are connected to receive water from the pressurized water container 5. However, the free ends of the water spray tubes 15 are closed.

A ring-shaped member 29 is provided at the other end of the barrel cavity 1. The ring-shaped member 29 has a radial extending opening formed therein that receives the compressed-air tube 30. The tube 30 can be readily inserted into or withdrawn from the radial extending opening by a swing-arm apparatus and electromagnetic presser 40 that is located on the upper portion of the barrel cavity 1.

The loading cover assembly includes an air-jet orifice-plate 23 having a plurality of air-jet apertures formed therein. An air-jet tube 24 is mounted at the center of the air-jet orifice-plate 23, and the object to be sterilized is arranged round the air-jet tub 24. The loading cover assembly further includes a heat isolating gasket 21, a cup-shaped joint 42, a heat isolating sealing sheet 25, a cavity cover 26 and a handle 20 all of which are fixed, in that order, to the air-jet orifice plate 23. A compressed-air joint 28 and a positioning pin 19 are located at a proper position on the periphery surface of the cup-shaped joint 42. When the loading cover assembly is positioned to cover and seal the barrel cavity 1, the positioning pin 19 fixes the position of the loading cover assembly and energizes the sensor 18. Energization of the sensor indicates that the cavity cover has been located in the proper position and it energizes a controlled circuit. Moreover, when the loading cover assembly is positioned to cover and seal the barrel cavity 1, the compressed-air tube 30 is connected with the compressed-air joint 28. In addition, when the loading cover assembly is positioned to cover and seal the barrel cavity 1, the cup-shaped joint 42 is located inside the inner of the ring-shape member 29, and the cavity cover 26 is provided on the flank of the ring-shape member 29.

Figure 2:
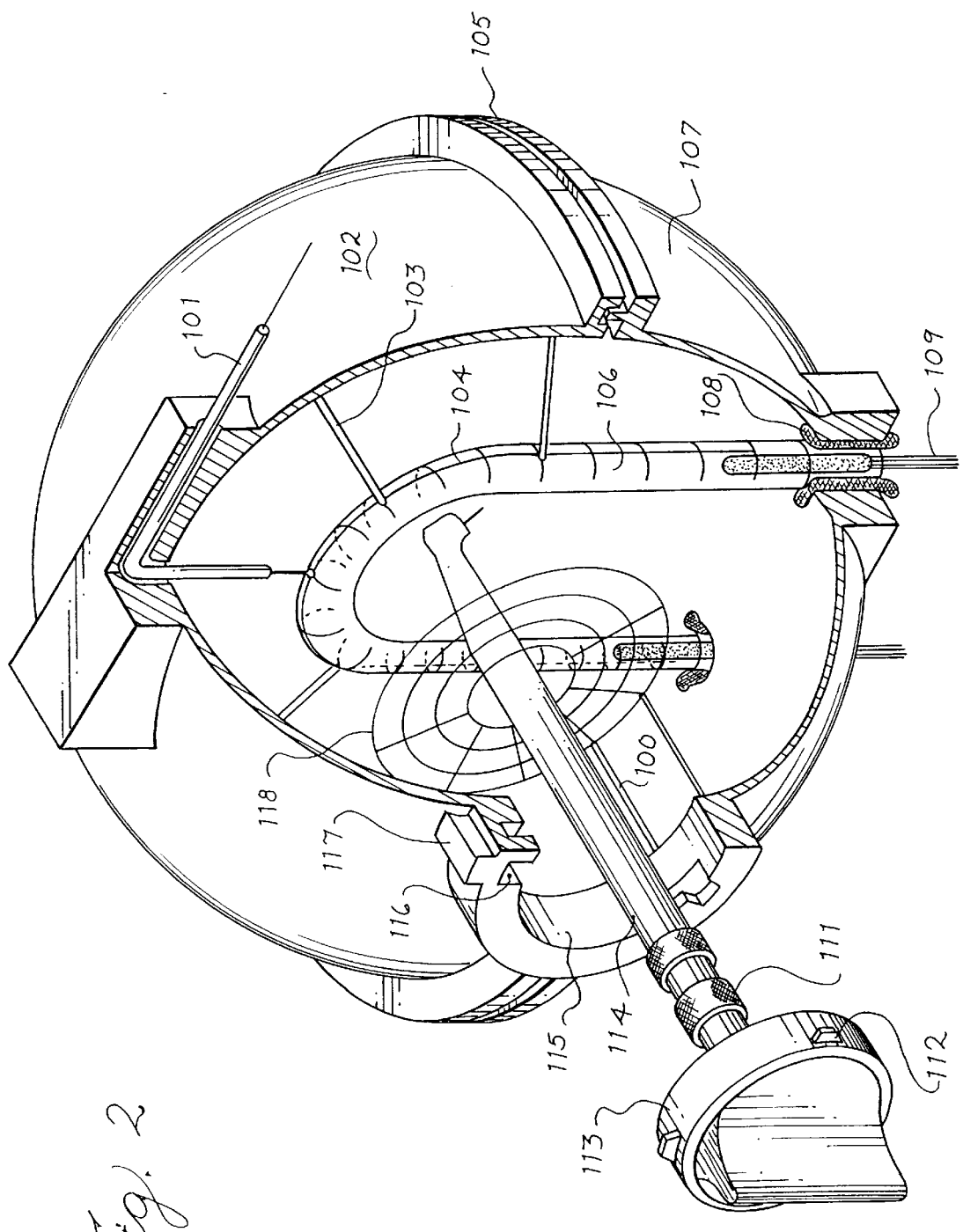
FIG. 2 is a partially cut-away-perspective-view of the integrated ball, that is used in the sterilization process.

Referring now to FIG. 2, the integrated ball for sterilization, comprises an upper semi-spherical cavity 102 and a lower semi-spherical cavity 107 which form a sphere when joined at a joint formed by their matching flanges. The inner surface of the spherical cavity is a high-reflectivity mirror surface. Inside the spherical cavity, a U-shaped tube 104 forms of pulse xenon lamp, for example, a pulse xenon lamp with repeated frequency. The U-shaped tube is fixed by several support rods 103. Two electrodes 109 of the lamp protrude away from the sphere. Heat resistant rubber sheets 108 are wrapped around the electrodes 109. The trigger high voltage connection 101 is led into the sphere from its upper portion and is connected with the upper portion of the U-shaped tube 104 of pulse xenon lamp.

The sphere has a cavity cap 113. In the center of the cavity cap 113, there is a movable intermediate joint 111 that extends in the axial direction and serves to mount the object to be sterilized. A number of positioning pins 112 are provided on the periphery surface of the cavity cap 113. The cavity cap 113 is sized to fit snugly in the cavity opening 115. In order to discharge the expanded gas from the sphere, an exhaust channel is arranged at the joint of the upper and the lower cavities 102, 107. A protecting net 118 that is fixed on supporting rods 100 is provided inside the spherical cavity.

To operate this apparatus, withdraw the loading cover assembly axially from the barrel cavity 1, as seen in FIG. 1. In doing so, the compressed-air tube 30 must be lifted slightly upwards. Arrange the object 16 to be sterilized around the center of the air-jet orifice-plate 23, then reset the loading cover assembly. The pressurized water and compressed-air are supplied to the water injecting tubes 15. The compressed-air cavity 22 is under the control of the control circuit illustrated in FIG. 3 as a result of the positioning pin 19 having reached its proper position. The object to be sterilized is washed by the injection of compressed-air and pressurized water. Next, under the control of the control circuit, heated compressed-air is supplied and the injection of pressurization water is stopped, and the object to be sterilized is dried. The object to be sterilized is taken from the barrel cavity 1 and is mounted on the movable intermediate joint 111 of the integrated ball for sterilization. The object to be sterilized is then put into the spherical cavity of the sphere, the pulse xenon lamp flashes a total of 6 times at intervals of one second between each flash. At this stage, under the action of the control circuit, the sterilizing process of the object has been completed.

The procedures for performing this sterilization method using laser pump source according to the present invention can be summarized as follows.

The first step is washing the object to be sterilized with pressurized water and compressed-air for about 30 seconds.

The second step is washing and drying the object to be sterilized with compressed-air of about 50° C. for about 30 seconds.

The third step is exposing the object to be sterilized to the irradiation of the pulse xenon lamp which flashes 6 times at intervals of one second between each flash.

The final step is warping the sterilized object with an aseptic jacket for storage and usage.

Another embodiment of this method and the apparatus for performing this method, according to the present invention, are the same as discussed above except that the laser pump source is a krypton lamp or a tungsten halide lamp.

This sterilization method and apparatus for performing the method not only thoroughly sterilizes precision and precious medical instruments, but also has the additional advantage that it shortens the time required for sterilization. This method and the apparatus used to perform this method are easy to operate and will not damage the instrument that is being sterilized. Furthermore, this method does not cause antigen to form.

What is claimed is:

1. A sterilization apparatus using a laser pump source comprising a control circuit, characterized in that the apparatus further includes a washing and drying means for washing and drying objects to be sterilized and an integrated ball for sterilization, wherein said washing and drying means includes:

a pressurization water source;

a compressed-air source and a compressed-air heater;

a barrel cavity having an opening, a ventilator on its upper side and a sewage outlet on its bottom side, wherein a number of water-spray-tubes are arranged at one end of the barrel cavity, said water-spray-tubes extending longitudinally and inwardly of said barrel cavity, said water-spray-tubes having a plurality of spray holes formed therein, the water spray tubes are connected to said pressurization water source;

said barrel cavity having an opening formed at another end;

a loading cover assembly is provided for closing said opening at the another end of the barrel cavity, which comprises an air-jet orifice-plate, a cup-shaped joint fixed with the air-jet orifice-plate, a handle for said loading cover assembly cover and a heat isolating gasket for sealing the heat in;

said air-jet orifice-plate has a plurality of air-jet apertures and an air-jet tube mounted in its center for arranging the object to be sterilized;

a compressed-air joint connected with a compressed-air source and a positioning pin for indicating that the loading cover assembly has been fixed and sealed in position are provided on the periphery of said cup-shaped joint;

a ring-shaped member having a radial through hole that is used for inserting the compressed-air tube and is located in a position corresponding to said compressed-air joint, during the fixed and sealed state, the cup-shaped joint and the air-jet orifice-plate of said loading cover assembly are arranged inside said inner side of said ring-shaped member; said compressed-air tube is inserted into said through hole by means of a swing-arm apparatus so as to be connected with the compressed-air joint;

said integrated ball for sterilization includes:
an upper semi-spherical and a lower semi-spherical cavities jointed together through a joint in a sealed manner to form a spherical cavity, a cavity opening located along said joint, a cavity cap having an outer and an inner surface and shaped to match said cavity opening, said cavity cap having a peripheral surface,
a laser pump source lamp is fixed inside the spherical cavity by several support rods, two electrodes of the lamp protrude outside the spherical cavity through the lower semi-spherical cavity, a trigger high voltage connection extends from the lamp through said spherical cavity; a handle is provided on the outer surface of the cavity cap, positioning pins are located on the peripheral surface of said cavity cap, and a movable intermediate joint extending axially from the inner surface of said cavity cap for mounting the object to be sterilized.

2. The apparatus according to claim 1, wherein said laser pump source is one of a pulse xenon lamp, a pulse krypton lamp or a pulse tungsten halide lamp.

* * * * *

UNITED STATES PATENT AND TRADEMARK OFFICE
CERTIFICATE OF CORRECTION

PATENT NO. : 6,013,070
DATED : January 11, 2000
INVENTOR(S) : Chuanlin Liu et al.

It is certified that error appears in the above-identified patent and that said Letters Patent is hereby corrected as shown below:

Under "[73] Assignees" change "Oingdao" (all three occurrences) to

-- Qingdao -- (all three occurrences).

Signed and Sealed this

Nineteenth Day of December, 2000

Attest:

Q. TODD DICKINSON

*Attesting Officer*  *Commissioner of Patents and Trademarks*